United States Patent
Ohtake et al.

(10) Patent No.: US 8,217,293 B2
(45) Date of Patent: *Jul. 10, 2012

(54) PROCESS AND SYSTEM FOR PRODUCING NUCLEAR SPIN POLARIZED XENON GAS

(75) Inventors: Norio Ohtake, Kawasaki (JP); Morio Murayama, Kawasaki (JP); Takashi Hiraga, Ikeda (JP); Mineyuki Hattori, Tsukuba (JP); Kazuhiro Homma, Tsukuba (JP)

(73) Assignees: Toyoko Kagaku Co., Ltd., Kanagawa (JP); National Institute of Advanced Industrial Science Technology, Tokyo (JP)

( * ) Notice: Subject to any disclaimer, the term of this patent is extended or adjusted under 35 U.S.C. 154(b) by 1844 days.

This patent is subject to a terminal disclaimer.

(21) Appl. No.: 10/541,704

(22) PCT Filed: Jan. 9, 2004

(86) PCT No.: PCT/JP2004/000093
§ 371 (c)(1),
(2), (4) Date: Jul. 8, 2005

(87) PCT Pub. No.: WO2004/063093
PCT Pub. Date: Jul. 29, 2004

(65) Prior Publication Data
US 2006/0083789 A1    Apr. 20, 2006

(30) Foreign Application Priority Data
Jan. 10, 2003   (JP) .................................. 2003-004304

(51) Int. Cl.
*B01J 19/12* (2006.01)
*B01J 19/14* (2006.01)
*B01D 5/00* (2006.01)
*G01R 33/26* (2006.01)

(52) U.S. Cl. ........... 204/157.22; 204/157.2; 204/157.21; 204/157.4; 204/157.41

(58) Field of Classification Search .. 204/157.2–157.22, 204/157.41, 157.15, 157.4
See application file for complete search history.

(56) References Cited

U.S. PATENT DOCUMENTS 2,712,384 A * 7/1955 Corneil ......................... 206/447
5,039,500 A * 8/1991 Shino et al. ................... 423/262

(Continued)

FOREIGN PATENT DOCUMENTS

JP       11-248809       9/1999

OTHER PUBLICATIONS

Jameson et al, "Nuclear Spin Relaxation by Intermolecular Magnetic Dipole Coupling in the Gas Phase, 129-Xe in Oxygen," J. Chem. Phys. 89 (7), Oct. 1, 1988, pp. 4074-4081.*

(Continued)

*Primary Examiner* — Keith Hendricks
*Assistant Examiner* — Colleen M Raphael
(74) *Attorney, Agent, or Firm* — Jordan and Hamburg LLP

(57) ABSTRACT

The present invention provides producing method and producing apparatus in which polarized xenon gas of high concentration is obtained without being frozen, and polarized xenon gas can be produced continuously. A glass cell having solid rubidium and solid xenon filled in vacuum is heated to be gas xenon and gas-liquid mixed rubidium, to which a magnetic field is applied to irradiate a laser beam thereby obtaining polarized xenon gas of high concentration.

12 Claims, 2 Drawing Sheets

U.S. PATENT DOCUMENTS

| | | | | |
|---|---|---|---|---|
| 5,545,396 | A | * | 8/1996 | Albert et al. .................... 424/9.3 |
| 5,617,860 | A | * | 4/1997 | Chupp et al. .................. 600/420 |
| 5,642,625 | A | * | 7/1997 | Cates et al. ..................... 62/55.5 |
| 5,809,801 | A | * | 9/1998 | Cates et al. ...................... 62/637 |
| 5,860,295 | A | * | 1/1999 | Cates et al. ...................... 62/637 |
| 5,934,103 | A | * | 8/1999 | Ryan et al. ....................... 62/637 |
| 6,079,213 | A | * | 6/2000 | Driehuys et al. ................. 62/3.1 |
| 6,085,743 | A | * | 7/2000 | Rosen et al. ............. 128/200.24 |
| 6,125,654 | A | * | 10/2000 | Honig .............................. 62/637 |
| 6,241,966 | B1 | * | 6/2001 | Albert et al. .................... 424/9.3 |
| 6,318,092 | B1 | * | 11/2001 | Happer et al. ................. 62/55.5 |
| 6,426,058 | B1 | * | 7/2002 | Pines et al. ..................... 424/9.3 |
| 6,523,356 | B2 | * | 2/2003 | Hasson et al. .................. 62/49.1 |
| 6,666,047 | B1 | * | 12/2003 | Shah et al. ....................... 62/637 |
| 6,942,467 | B2 | * | 9/2005 | Deninger et al. ............. 417/313 |
| 7,287,390 | B2 | * | 10/2007 | Bolam ........................... 62/55.5 |
| 7,541,051 | B2 | * | 6/2009 | Hattori et al. ................. 424/600 |
| 2006/0173282 | A1 | * | 8/2006 | Ardenkjaer-Larsen et al. ............................ 600/420 |

OTHER PUBLICATIONS

Frossati, "Polarization of 3-He, D2, (and possibly 129-Xe) Using Cryogenic Techniques," Nucl. Instr. and Methods in Phys. Research A 402 (1998) pp. 479-483.*

Zook et al, "High Capacity Production of >65% Spin Polarized Xenon-129 for NMR Spectroscopy and Imaging," J. Mag. Res. 159 (2002) pp. 175-182.*

Properties of Pure Metals, Properties and Selection: Nonferrous Alloys and Special-Purpose Materials, vol. 2, ASM Handbook, ASM International, 1990, p. 1099-1201.*

Bowers et al, "Cross polarization from laser-polarized solid xenon to 13CO2 by low-field thermal mixing," Chem. Phys. Lett. 205 (2,3), pp. 168-170.*

Song, Y-Q., "Spin Polarization-Induced Nuclear Overhauser Effect: An Application of Spin-Polarized Xenon and Helium," Concepts in Mag. Res., 12(1) pp. 6-20 (2000).*

Happer et al, "Polarization of the nuclear spins of noble-gas atoms by spin exchange with optically pumped alkali-metal atoms," Phys. Rev. A, 29 (6), Jun. 1984, pp. 3092-3110.*

Oct. 15, 1989 Optical pumping of high-density Rb with a broadband dye laser and GaAlAs diode laser arrays: Application to $^3$He polarization M.E. Wagshul & T.E. Chupp The American Physical Society vol. 40, No. 8 pp. 4447-4454.

Feb. 4, 1991 High-Field NMR of Adsorbed Xenon Polarized by Laser Pumping D. Raftery, et al. The American Physical Society vol. 66, No. 5 pp. 584-587.

Jul. 8, 1996 High-Volume production of laser-polarized $^{129}$Xe B. Driehuys et al. American Institute of Physics, Appl. Phys. Lett. vol. 69 pp. 1668-1670.

* cited by examiner

PROCESS AND SYSTEM FOR PRODUCING NUCLEAR SPIN POLARIZED XENON GAS

BACKGROUND

This invention relates to a method and apparatus for producing nuclear spin polarized xenon gas, and more specifically, relates to continuously producing highly concentrated nuclear spin polarized xenon gas capable of producing a polarized nuclear spin useful for NMR+MRI apparatus.

It has been recently reported that when xenon gas with a nuclear spin polarized (nuclear spin polarized xenon gas) is applied to NMR·MRI method, detection sensitivity is enhanced rapidly.

The term 'polarized' as used herein means that distribution of the spin number occupying energy order of nuclear spins of an atomic nucleus corresponding to the orientation state with respect to the metal static magnetic field is extremely one-sided.

To obtain a rare gas having the polarized state circularly polarized excitation light is irradiated on gas having rare gas including a single atomic molecule having a nuclear spin of spin quantum number 112 such as xenon-129 ($^{129}Xe$), helium-3 ($^{9}He$) or the like mixed with alkali metal vapor such as rubidium, cesium or the like. An electron in the base state order of rubidium or the like is excited by light absorption in the base state order and returned to the base state order after passage of the base state order, at which time it is transited with high probability to one order of electron orders out of the base state orders whose degeneracy is released magnetically by a magnetic field. The magnetic field is applied from outside to prepare the state that an electronic spin polarization degree of a rubidium molecule or the like is high, and the rubidium or the like in the high polarization state collides with rare gas such as xenon, at which channel the high polarization state of rubidium or the like moves to a nuclear spin system of rare gas such as xenon. This channel is generally called optical pumping.

In the conventional polarized rare gas producing apparatus, a mixed gas of rare gas and alkali metal vapor is confined into an optical reaction vessel, to which irradiation of excited light and application of magnetic field are carried out. For example, there is a producing apparatus, for the purpose of using polarized helium-3 of high density as a neutral polarizer, in which a mixed gas of helium-3 gas and nitrogen gas and alkali metal are confined into a cylindrical glass ample (for example, see M. E. Wagshul and T. E. Chu P P, Phy, Rev. A40, 4447 (1989)).

On the other hand, there is an apparatus in which for example, 1% of xenon is mixed with buffer gas of helium of 10 atmospheric pressure or so, introduced into a cylindrical glass vessel, irradiated, polarized, and guided into Dewar cooled by liquid nitrogen from a gas outlet of the vessel. Polarized xenon is formed into a solid, which is separated. The remaining helium gas is discharged from a vent line (For example, see B. Driehuys, G. D. Cates, E. Miron, K. Sauer, D. K. Walter and W. Happer, Appl. Phys, Lett. 69, 1668 (1996).

In any of those apparatuses as noted above, operation for enhancing the polarization rate is carried out by receiving a laser beam in the state that rare gas or the like is stayed in an optical reaction vessel. With the polarization rate enhanced, and after the temperature cooled to a room temperature, the gas may be used as a neutral polarizer as it is, or polarized as xenon 129 once solid-separated within Dewar is heated again into gas. Then it is transferred to a separate vessel for use in measurement of NMR or the like.

However, in the above-mentioned conventional method, for facilitating polarization, xenon is diluted, for example, to helium 2% xenon concentration or so. Polarized gas containing produced xenon then is frozen with liquid nitrogen, which is heated to remove only the xenon to produce high concentration xenon gas, thus posing a problem that work efficiency is extremely poor. In addition, in the conventional apparatus in which gas or the like is stayed and polarized, since polarized gas cannot be generated continuously, polarized gas is taken out into a separate vessel every time and carried to NMR apparatus, thus taking time, and posing a problem that the polarization rate reduces during such a period of time as described.

This invention has been accomplished in view of the foregoing, and has its object to provide producing method and producing apparatus capable of obtaining polarized xenon gas of high concentration without being frozen, and capable of generating polarized xenon gas continuously.

It is a further object of this invention to provide producing method and producing apparatus of a glass cell in which metal rubidium and xenon gas used for the above-described producing method and producing apparatus are solidified and sealed under the absence of oxygen.

SUMMARY OF THE INVENTION

A glass cell having solid rubidium and solid xenon filled in the pressure reducing state of being absent in oxygen is heated to be gas xenon and gas-liquid mixed rubidium, to which a magnetic field is applied to irradiate a laser beam. It is noted that being absent in oxygen termed herein is meant not to oxidize solid rubidium, and the presence of a fine amount of oxygen to a degree that even if solid rubidium is oxidized, reaction is not affected, is allowed.

When the thus produced nuclear spin polarized xenon gas is taken out, pressure naturally lowers and air flows backward into the glass cell. Therefore, xenon polarized gas is taken out while introducing xenon gas so as to maintain fixed pressure. Further, by doing so, polarized xenon gas can be produced continuously.

Preferably, it is constituted so that in replacing a xenon gas supply device, the xenon gas supply device side is made to be a primary side through a first air operate valve, and the xenon gas introducing side of the glass cell is made to be a secondary side, and vacuuming of the primary side piping and pressurization-leaving by nitrogen gas are repeated automatically more than three times.

Preferably, in replacing the glass cell, vacuuming of piping from the primary side piping, the secondary side pipe and the primary side pipe to a valve on the polarized xenon gas take-out side communicated through a second air operate valve and pressurization-leaving by nitrogen gas are repeated automatically more than three times.

To produce a glass cell according to the present invention a chamber houses a glass vessel filled with rubidium. The chamber and said glass cell are connected so that they are in communication by piping. The piping is exhausted by a vacuum generator, after which the glass vessel filled with rubidium is broken, and the metal rubidium, piping and glass cell heated. As a result rubidium gas is made present within the piping and glass cell. Then the glass cell is cooled, metal rubidium is precipitated as a solid into the cooled portion, xenon gas is introduced into the glass cell and closed, and the glass cell is cooled to solidify xenon within the glass cell.

An apparatus for carrying out the present invention, includes means for heating a glass cell having solid rubidium and solid xenon filled in the pressure reducing state, in which oxygen is absent, to achieve gas xenon and gas-liquid mixed rubidium, and means for applying a magnetic field to the glass cell to irradiate a laser beam.

Further, preferably, there comprises means for introducing xenon gas while taking out the produced nuclear spin polarized xenon gas, and pressure regulating means for controlling said operation so that pressure may not drop.

Piping from a xenon gas supply to a first air operate valve serves as primary side piping. Piping from such first air operate valve to a valve for introducing xenon gas into the glass cell serves as secondary side piping. Provided on the primary side are branched pipings and pressure regulating means. The branched pipings are connected to said primary side piping through a second air operate valve. One of said branched pipings reaches a vacuum generator and another reaches a valve on the xenon gas taking-out side of said glass cell. The pressure regulating means regulates pressure introduced into the glass cell.

An apparatus for producing a glass cell according to the present invention includes piping connected so that a chamber housing rubidium filled into a glass vessel and the glass cell are connected. Also included are means for vacuuming the piping, means for breaking glass having rubidium filled in, means for heating the metal rubidium, piping and glass cell, and means for cooling the glass cell and precipitating metal rubidium on the cooled portion.

In summary, the gist of the present invention lies in that xenon is filled into the glass cell having metal rubidium adhered thereto heated to irradiate a laser beam thereby obtaining polarized xenon gas of high concentration without being frozen.

DETAILED DESCRIPTION

In the following, the embodying form of the present invention will be described with reference to the drawings.

Figure 1:
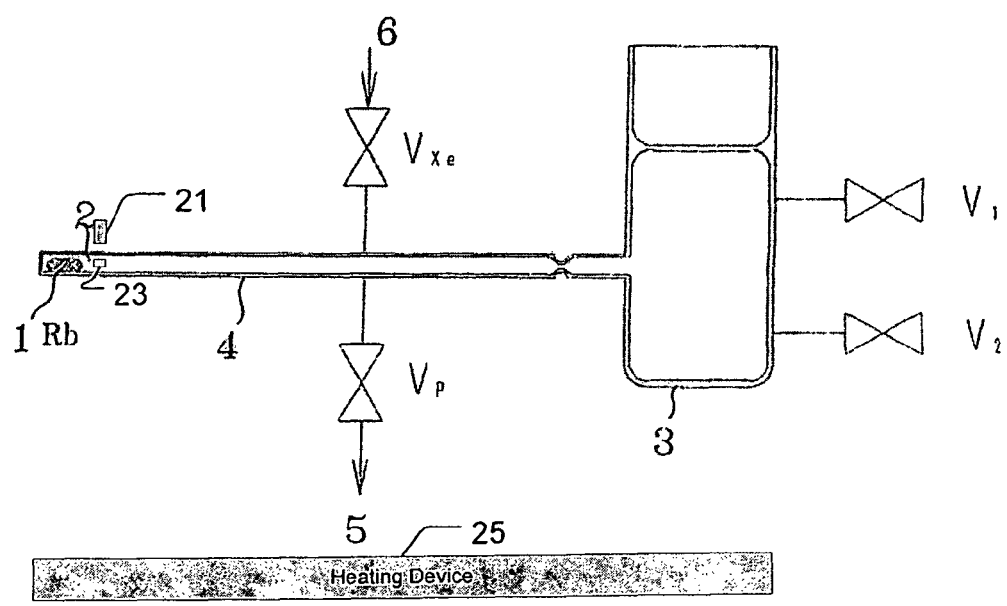
FIG. 1 is a schematic sectional view showing a producing apparatus of a glass cell having rubidium and xenon filled therein according to the present invention.

FIG. 1 shows a glass cell having rubidium and xenon filled in, in which a vacuum pump 5 and a xenon gas supply line 6 are connected to piping 4 connecting a metal rubidium 1 enveloped with glass housing chamber 2 and a glass cell 3. When rubidium comes in contact with air, it is oxidized and changed into oxide of rubidium, and therefore in case of purchasing it from makers, it is filled in glass as described above. It is noted that in this state, a valve Vxe, a valve V1 and a valve V2 are closed.

If a valve Vp is opened, in the state that the valve Vxe is closed, to exhaust by the vacuum pump 5, air in the piping 4 and the glass cell 3 is exhausted. When, in this state, glass in which rubidium is filled is broken, metal rubidium will be present in vacuum, thus not being oxidized. A magnet 21 enveloped with glass is also filled in the metal rubidium 1 housing chamber 2. The magnet 21 is moved by a magnet 23 from outside into contact with metal rubidium 1 to break the glass.

Next, the metal rubidium 1, glass cell 3 and piping 4 are wholly heated by a heating device 25. It is suggested that a heating temperature is not less than a melting point (about 40° C.) of rubidium, and is a temperature that rubidium assumes a gas-liquid mixed state in which liquid and gas of a vapor pressure portion at that temperature are present with high concentration. More specifically, preferably, 130-180° C., particularly preferably, near 150° C.

Figure 3:
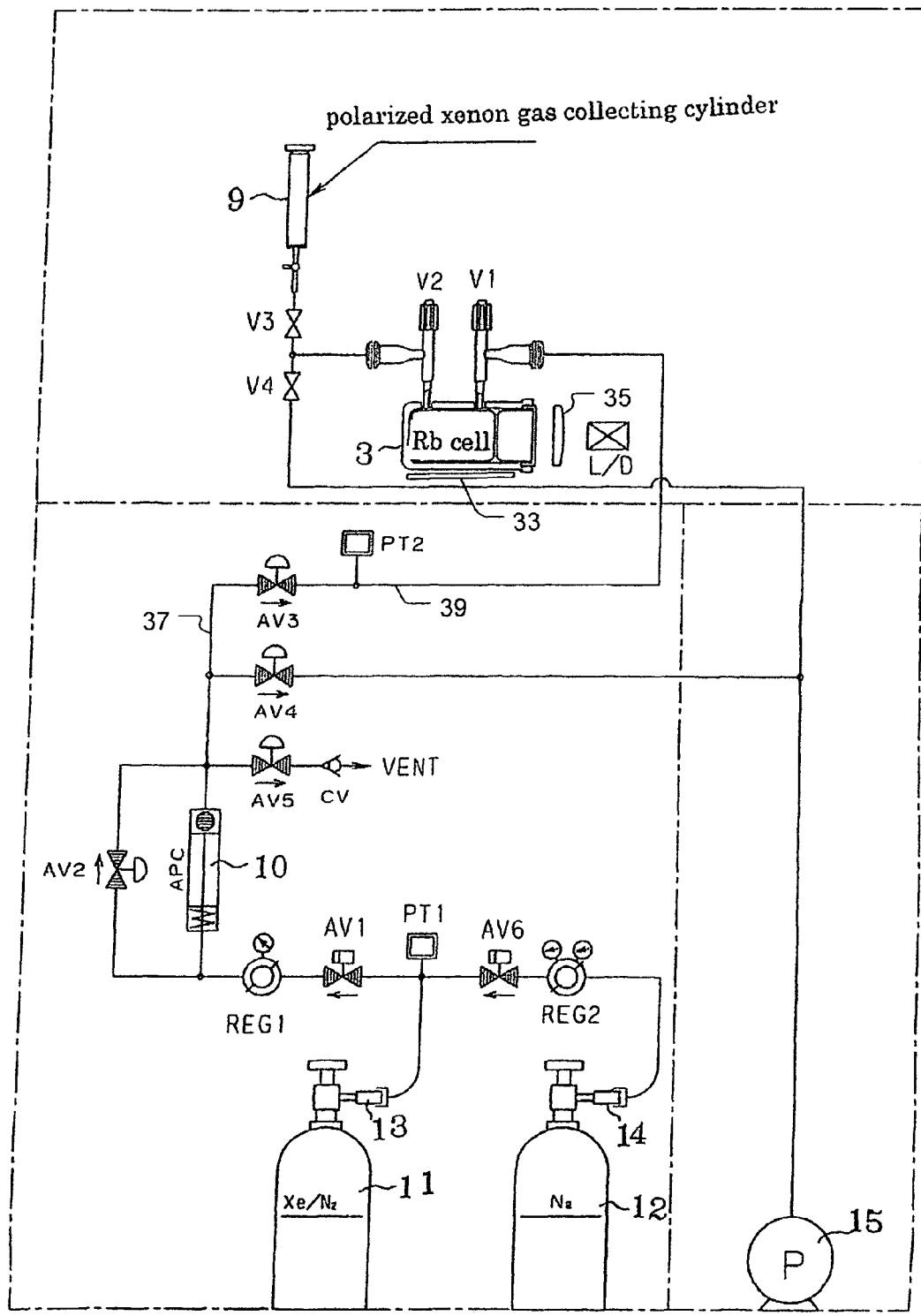
FIG. 3 is a structural view showing one embodiment of the producing apparatus according to the present invention.

Then, when only a part of glass cell is cooled, rubidium in the gas state is solidified on only the cooled part and separated as shown in FIG. 3.

Then, when the vacuum pump 5 side valve Vp is closed and Vxe is opened, gaseous xenon is introduced into the glass cell 3. Next, when Vxe is closed, and the whole glass cell 3 is cooled with liquid nitrogen, xenon is turned to solid. Originally, since xenon is introduced into solid rubidium confined in vacuum, if xenon is solidified, the glass cell assumes a pressure reducing state (vapor pressure at a liquid nitrogen temperature).

Figure 2:
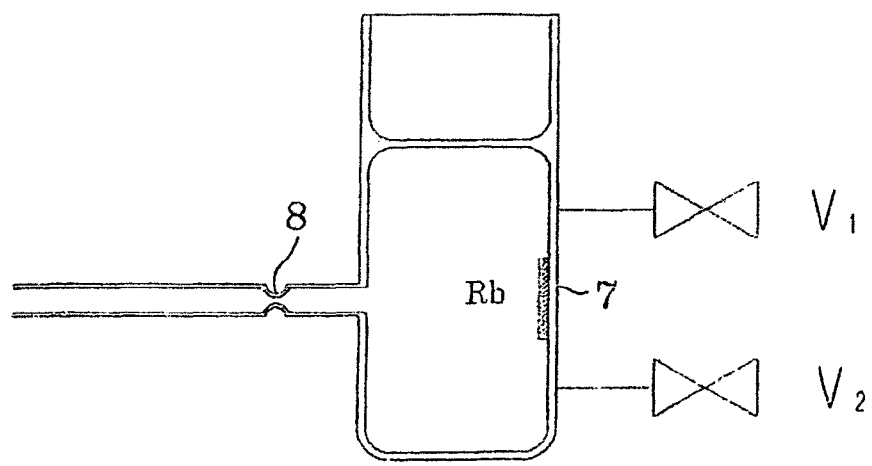
FIG. 2 is a sectional view showing the state that rubidium and xenon are filled in, and thereafter a glass cell is closed and sealed.

In this state, if a portion 8 depicted in FIG. 2 is heated and molten by operation of a burner, the glass cell 3 having solid rubidium and solid xenon filled in is obtained. The glass cell then may be used in a system as shown in FIG. 3 to produce the polarized zenon gas.

Referring to FIG. 3, when a heating device 33 heats the glass cell 3 to elevate the temperature of the glass cell 3, preferably, to 50-180° C., particularly preferably, near 120° C., the glass cell contents will internally become xenon gas and gas-liquid mixed rubidium. In this state, if a magnetic field is applied by a magnetic source 35 to irradiate laser, xenon gas will be nuclear spin polarized xenon gas in scores of minutes.

Referring to FIG. 3, when the valves V2 and V3 are opened, polarized xenon gas is collected by a polarized xenon gas collecting cylinder 9. At the same time, the valve V1 may be opened to introduce xenon gas while regulating pressure by an auto pressure regulator (APC) 10, so that pressure may not drop. When polarized xenon gas in the glass cell 3 is taken out, pressure lowers and the air back flows, because of which the pressure-regulate xenon gas is introduced as described above. It is noted that in this state, air operate valves AV6, AV 1 and AV3, and valves V1. V2 and V3 in FIG. 3 are opened.

Then, the valves V1 and V2 are closed, the whole glass cell 3 is cooled with liquid nitrogen, and after xenon is solidified. The glass cell 3 then is heated to produce polarized xenon gas by the same operation as mentioned above. In this manner, it can be produced repeatedly continuously till rubidium as a catalyst is gone.

As also shown in FIG. 3, xenon gas from a xenon cylinder 11 may be introduced from the valve V1 of the glass cell 3 passing though an air operate valve (AV 1), an auto pressure regulator (APC) 10 and a first air operate valve (AV3). In this embodiment, since pressure for taking out polarized xenon gas is 1.5 atmospheric pressure or so, pressure of xenon gas is regulated to the same 1.5 atmospheric pressure or so by APC 10. In FIG. 3, valves V1-V4 are constituted by glass valves because polarized gas comes in contact, and because if glass is not employed, polarized xenon gas returns to xenon gas. Accordingly, other portions within piping with which polarized xenon gas contacts are also glass (pyrex).

Nitrogen gas and xenon gas are dropped down to pressure of 1.5 atmospheric pressure or so by pressure reducing valves (REG 2 and REG 1), respectively.

In the above-described reaction, it is necessary that air may not enter at all the glass cell. Because even if a small amount of air is mixed, the rubidium catalyst is oxidized, resulting in not exhibiting the catalyst function.

Air is mixed in at the time of replacing a cylinder and at the time of replacing a glass cell, in which case, air is prevented from mixing into the glass cell in the following manner.

In case of replacing a xenon cylinder, air is mixed into piping between an original valve 13 of the cylinder, an air operate valve (AV 1) and an air operate valve (AV6). For removing the air, a vacuum pump (P) 15 is turned on, an air operate valve (AV 1) and air operate valve (AV2) and a second operate valve (AV4) are opened to vacuum piping on the primary side, and the state is left as it is for a fixed time while detecting a pressure reducing degree by a pressure transmitter ((PT1). Through the first air operate valve (AV3), the xenon gas supply device side is made to be a primary side, and the xenon gas introducing side of the glass cell is made to be a secondary side. Piping between the introducing valve at the glass cell 3 and the first air operate valve (AV3) is referred to herein as secondary side piping 39. Piping between the xenon gas supply device 11 and the first air operate valve is referred to herein as primary side piping 37.

Then, the second air operate valve (AV4) is closed to pressurize the interior of piping on the primary side with nitrogen gas. The pressure on the primary side is left for fixed time preset while detecting it by the pressure transmitter (PT 1). Then, the step is again repeated for vacuuming again the interior of piping on the primary side and pressurizing the interior of piping on the primary side with nitrogen gas to leave it. Preferably, it is possible to prevent oxygen from mixing into the glass cell by repeating the step more time 10 times.

When the glass cell is replaced, air is mixed into the piping between piping to the manual valve V1 at a glass cell inlet on the secondary side in communication with piping on the primary side through the first air operate valve (AV3), the manual valve V2 for taking out polarized gas, the valve V3 or controlling the flow into the collecting portion, and the valve V4 for controlling the communication with the vacuum pipe.

The valve V4 and the second air operate valve (AV4) (controlling communication between piping on the primary side and the vacuum pump) are opened to vacuum the interior of piping of the air mixing portion. Then, the first air operate valve from the both cylinder 11,12 (AV3) connecting pipings on the primary side and secondary side, and the valve to the first air operate valve (AV3) are opened to pressurize piping on the primary side and piping on the secondary side with nitrogen gas, and all the valves are closed for pressurization-leaving. Then, the step is repeated for opening the first air operate valve and the second air operate valve, vacuuming similar to that mentioned above, and pressurization-leaving. Preferably, it is possible to prevent oxygen from mixing into the glass cell by repeating the step more than 10 times. Since the pressure transmitter (PT2) is disposed on piping on the secondary side, vacuuming and pressurization-leaving are performed for fixed time pre-set while sensing pressure. The air operate valve (AV5) in FIG. 3 is a valve for releasing gas when the interior of the primary piping is in the pressurizing state, which is however not used in the above-described operation.

In FIG. 3, while nitrogen and xenon gas are supplied from the cylinder, well known other gas supply devices will suffice.

According to the present invention, reaction is done with high concentration such as xenon gas 80-100% (remainder, nitrogen gas) to thereby obtain polarized xenon gas, thus obtaining polarized xenon gas of high concentration without carrying out treatment such as solidifying after being polarized.

Further, vacuuming the interior of piping and pressurization-leaving can be carried out many times to prevent air from flowing into the glass cell.

As described above, according to the present invention, since xenon gas of high concentration can be used to produce polarized xenon gas of high concentration, trouble of concentrating by freezing after production as in prior art can be eliminated.

Further, xenon gas as raw material is regulated in pressure and introduced while taking out polarized xenon gas, whereby back-flow of air is prevented, and polarized xenon gas can be produced continuously.

Furthermore, vacuuming the interior of piping and pressurization-leaving are carried out repeatedly to thereby sufficiently enable purging the interior of piping, and so, it is possible to prevent mixing of air in the reaction glass cell, and to extend the life of the rubidium catalyst.

Accordingly, it is expected to utilize the invention as producing method and producing apparatus of producing polarized nuclear spin polarized xenon gas useful for NMR·MRI apparatus with high concentration and continuously.

The invention claimed is:

1. A method for producing nuclear spin polarized xenon gas, comprising:
   coupling piping to a sealed glass cell, filled with solid material consisting of solid rubidium and solid xenon, during which the sealed glass cell becomes unsealed, wherein said sealed glass cell is in a pressure reducing state of being absent of oxygen;
   heating the glass cell filled with solid rubidium and solid xenon in the pressure reducing state of being absent in oxygen to produce therein gaseous xenon and a mixture of gas and liquid phases of rubidium;
   irradiating with a laser beam the gaseous xenon and the mixed-phase rubidium that is in the glass cell and is produced from the solid xenon and solid rubidium, and
   applying a magnetic field to the irradiated gaseous xenon and mixed-phase rubidium in the glass cell to achieve the nuclear spin polarized xenon gas, wherein nuclear spin polarized xenon gas is achieved at a concentration of at least 80% by said heating, irradiating and applying without a need for subsequent freezing to achieve said concentration.

2. The method of claim 1, further comprising:
   removing nuclear spin polarized xenon gas from the glass cell; and
   during said removing, introducing gas into the glass cell in a manner that maintains fixed pressure within the glass cell, wherein said introduced gas consists of at least 80% xenon gas and a remainder percentage of nitrogen gas.

3. The method of claim 2, wherein said introduced gas is introduced from a xenon gas supply device into the glass cell along primary side piping, located between the xenon gas supply device and a first air operate valve, and second side piping, located between the first air operate valve and the glass cell; and further comprising:
   replacing the xenon gas supply device while the glass cell is coupled to the secondary side piping and to outlet piping;
   vacuuming the primary side piping; and
   pressurizing the primary side piping with nitrogen gas, wherein the vacuuming and pressurizing are repeated automatically at least three times after the replacing.

4. The method of claim 2, wherein said introduced gas is introduced from a xenon gas supply device into the glass cell along primary side piping, located between the xenon gas supply device and a first air operate valve, and second side piping, located between the first air operate valve and the glass cell; wherein nuclear spin polarized xenon gas is removed from the glass cell through outlet piping, and wherein branch piping connects between a valve at the outlet piping and a second air operate valve coupled to the primary side piping, and further comprising:
- replacing the glass cell with another glass cell filled with solid rubidium and solid xenon;
- opening the first and second air operate valves and the valve at the outlet piping;
- vacuuming the primary side piping, secondary side piping, and branch piping;
- pressurizing the primary side piping, secondary side piping, and branch piping with nitrogen gas; and
- closing the first and second air operate valves and the valve at the outlet Piping;
- wherein the opening, vacuuming, pressurizing, and closing are repeated automatically at least three times after the replacing.

5. The method of claim 2, further comprising:
- after said removing and introducing, isolating the glass cell to prevent entry or exit of contents;
- cooling the isolated glass cell sufficiently to solidify xenon gas content; and
- repeating the steps of removing and introducing.

6. The method of claim 1, wherein said heating, irradiating, and applying produce a highly concentrated, spin-polarized xenon gas in the glass cell, and wherein output from the glass cell may be used in an NMR/MRI process without first being frozen.

7. A method of producing a glass cell filled with solid rubidium and solid xenon in a vacuum from glass encased rubidium located in a chamber, the chamber coupled to the glass cell by piping, the method comprising:
- exhausting the piping with a vacuum generator;
- breaking the glass that encases the rubidium;
- heating the rubidium, the piping and the glass cell causing rubidium to enter into a gaseous state, wherein the gaseous rubidium enters the glass cell;
- cooling the glass cell causing rubidium to precipitate as a solid within the glass cell; and isolating the glass cell to include rubidium in a vacuum;
- after said isolating, the method of producing a glass cell filled with solid rubidium and solid xenon in a vacuum consisting of:
- filling the glass cell having solid rubidium with xenon gas; isolating the filled glass cell having solid rubidium and xenon gas within the glass cell; and
- cooling the isolated glass cell causing xenon within the glass cell to solidify and the glass cell to assume a pressure reducing state.

8. An apparatus for producing nuclear spin polarized xenon gas, comprising:
- a sealed glass cell filled with solid material consisting of solid rubidium and solid xenon in a pressure reducing state of being absent of oxygen;
- an inlet valve coupled to the sealed glass cell and an outlet valve coupled to the glass cell, wherein upon opening of either one or of the inlet valve or outlet valve the glass cell becomes unsealed;
- means for heating the glass cell filled with solid rubidium and solid xenon in the pressure reducing state of being absent in oxygen to produce therein gaseous xenon and a mixture of gas and liquid phases of rubidium;
- a laser projecting a beam into the glass cell for irradiating the gaseous xenon and the mixed-phase rubidium; and
- means for applying a magnetic field to the irradiated gaseous xenon and mixed-phase rubidium to achieve the nuclear spin polarized xenon gas, wherein nuclear spin polarized xenon gas is achieved at a concentration of at least 80% by said heating, irradiating and applying without a need for subsequent freezing to achieve said concentration.

9. The apparatus of claim 8, further comprising:
means for introducing xenon gas while taking out the produced nuclear spin polarized xenon gas; and
pressure regulating means for maintaining a fixed pressure within the glass cell while gas is being introduced and nuclear spin polarized xenon gas is being taken out, said introduced gas consisting of at least 80% xenon gas and a remainder percentage of nitrogen gas.

10. The apparatus of claim 9, further comprising:
means for isolating the glass cell to prevent entry or exit of contents; and
means for cooling the isolated glass cell sufficiently to solidify xenon gas content.

11. The apparatus of claim 8, further comprising:
a xenon gas supply device;
a first air operate valve;
primary side piping coupling the xenon gas supply device to the first air operate valve;
second side piping coupling the glass cell to the first air operate valve;
pressure regulating means;
a second air operate valve coupled to the primary side piping;
outlet piping coupling the glass cell to an outlet;
a third valve coupled to the outlet piping; and
branch piping coupled to the second air operate valve, the branch piping having a first branch coupled to the third valve and having a second branch coupled to a vacuum generator.

12. An apparatus for producing a glass cell having solid rubidium and solid xenon in a vacuum therein, comprising:
a chamber housing glass encased rubidium;
piping coupling the chamber and a glass cell;
a vacuum generator coupled to the piping for evacuating the piping and glass cell;
means for breaking the glass that encases the rubidium, exposing the rubidium to a vacuum;
means for heating the rubidium, the evacuated piping and the evacuated glass cell causing rubidium to enter into a gaseous state, wherein the gaseous rubidium enters the glass cell;
means for cooling the glass cell causing rubidium to precipitate as a solid within the glass cell;
means for filling the glass cell having solid rubidium with xenon gas; and
means for cooling the filled glass cell causing xenon within the glass cell to solidify and the glass cell to assume a pressure reducing state absent of oxygen while content in the glass cell consists of solid rubidium and solid xenon.

* * * * *